United States Patent [19]

Hauschild

[11] Patent Number: 5,676,933
[45] Date of Patent: *Oct. 14, 1997

[54] STABLE SODIUM PERCARBONATE FORMULATION

[75] Inventor: John P. Hauschild, Bridgewater, N.J.

[73] Assignee: Church & Dwight Co., Inc., Princeton, N.J.

[*] Notice: The term of this patent shall not extend beyond the expiration date of Pat. No. 5,374,368.

[21] Appl. No.: 502,212

[22] Filed: Jul. 13, 1995

Related U.S. Application Data

[60] Division of Ser. No. 300,057, Sep. 2, 1994, Pat. No. 5,496,542, which is a continuation-in-part of Ser. No. 142,856, Oct. 25, 1993, Pat. No. 5,374,368.

[51] Int. Cl.$^6$ .............................. A61K 7/20; A61K 7/16
[52] U.S. Cl. .................... 424/53; 424/49; 424/57
[58] Field of Search ................................ 424/49–58

[56] References Cited

U.S. PATENT DOCUMENTS

| | | | |
|---|---|---|---|
| 4,891,211 | 1/1990 | Winston | 424/53 |
| 4,925,655 | 5/1990 | Smigel | 424/53 |
| 4,971,782 | 11/1990 | Rudy et al. | 424/53 |
| 5,180,576 | 1/1993 | Winston et al. | 424/52 |
| 5,215,740 | 6/1993 | Domke et al. | 424/52 |
| 5,256,402 | 10/1993 | Prencipe et al. | 424/53 |
| 5,294,432 | 3/1994 | Winston et al. | 424/52 |
| 5,374,368 | 12/1994 | Hauschild | 424/53 |
| 5,376,360 | 12/1994 | Domke et al. | 424/52 |
| 5,424,460 | 6/1995 | Hauschild | 424/53 |
| 5,456,903 | 10/1995 | Hueter | 424/53 |
| 5,496,542 | 3/1996 | Hauschild | 424/53 |

*Primary Examiner*—Shep K. Rose
*Attorney, Agent, or Firm*—Irving M. Fishman

[57] ABSTRACT

This invention provides a stable hydrogen peroxide-releasing formulation in liquid or gel form, having a content of sodium percarbonate which is stabilized by a specific proportion of deionized water. The formulation ingredients can be incorporated in detergent or dentifrice compositions, and the sodium percarbonate ingredient exhibits long term stability during manufacture and storage of the compositions.

6 Claims, 3 Drawing Sheets

STABLE SODIUM PERCARBONATE FORMULATION

CROSS-REFERENCES

This patent application is a divisional patent application of patent application Ser. No. 08/300,057 filed Sep. 2, 1994 (now U.S. Pat. No. 5,496,542), which is a continuation-in-part of patent application Ser. No. 142,856 filed Oct. 25, 1993 (now U.S. Pat. No. 5,374,368).

The subject matter of this patent application is related to that disclosed in commonly assigned U.S. Pat. Nos. 4,891,211; 5,180,576; 5,215,740; 5,294,432; 5,374,368; 5,376,360; 5,424,060; and 5,496,542.

BACKGROUND OF THE INVENTION

Sodium carbonate forms a crystalline addition compound with hydrogen peroxide, corresponding to the formula 2 $Na_2CO_3 \cdot 3\ H_2O_2$ (sodium carbonate sesquiperoxide), and is commonly known as sodium percarbonate. The compound has many potential applications as a peroxygen source when dissolved in an aqueous medium.

Sodium percarbonate has a high active oxygen content (15.28% theoretical) and high water solubility. It is produced from low cost starting materials, and it is an environmentally safe chemical.

Sodium percarbonate has not achieved the commercial acceptance of sodium perborate, mainly because it is less stable than sodium perborate. Solid sodium percarbonate decomposes with a loss of active oxygen which is substantially greater than the decomposition of sodium perborate under the same conditions. This problem is particularly undesirable in detergent cartons sold at retail. The problem also is evident during processing and storage of detergent compositions.

Stabilizers such as magnesium sulfate are suitable for stabilizing sodium perborate, but provide only limited protection with sodium percarbonate. Various methods for stabilization of sodium percarbonate have been proposed.

U.S. Pat. No. 2,380,620 discloses that sodium silicate, magnesium sulphate or gum arabic are unsatisfactory stabilizers when incorporated in sodium percarbonate, but diphenylguanidine lessens the decomposition in the presence of the conventional stabilizers.

U.S. Pat. No. 3,951,838 discloses that prior attempts at chemical stabilization of sodium percarbonate, primarily by magnesium silicate, are generally ineffective in promoting long term stability, particularly in a humid atmosphere. The patent proposes coating of the particles with an aqueous silica sol and drying to accomplish stabilization.

U.S. Pat. No. 4,075,116 describes cocrystallizing of sodium percarbonate with other salts known to form perhydrates such as sodium sulfate, sodium pyrophosphate, sodium glucoheptonate, sodium perborate, and the like.

U.S. Pat. No. 4,171,280 discloses that a non-caking bleach composition may be formed containing up to 6% active oxygen by spraying only sufficient hydrogen peroxide onto sodium carbonate particles to convert a part of the sodium carbonate to sodium percarbonate. U.S. Pat. No. 4,260,408 teaches the addition of sodium phosphate to the composition as a stabilizer. Both patents demonstrate that an assay of less than 6% active oxygen (less than 40% sodium percarbonate) is necessary to obtain satisfactory stability.

U.S. Pat. No. 5,244,644 describes a process for producing alkali metal percarbonate with improved caking resistance which involves admixing percarbonate powder with a particulate fatty acid metal salt additive.

There is continuing research and development effort to produce sodium percarbonate in a form which exhibits long term stability under storage conditions, and when incorporated as a peroxygen ingredient in commercial products.

Accordingly, it is an object of this invention to provide a sodium percarbonate formulation which is stable under ambient temperature and moisture conditions.

It is a further object of this invention to provide a sodium percarbonate formulation which is stable when incorporated as an ingredient in a detergent or dentifrice type consumer product, and which releases active oxygen under product utilization conditions.

Other objects and advantages of the present invention shall become apparent from the accompanying description and examples.

DESCRIPTION OF THE INVENTION

One or more objects of the present invention are accomplished by the provision of a stable hydrogen peroxide-releasing formulation comprising (1) between about 55–90 weight percent of polyalkylene glycol; (2) between about 5–20 weight percent of sodium percarbonate; (3) between about 0.5–6 weight percent of colloidal silica; (4) between about 0–12 weight percent of alkali metal pyrophosphate; and (5) between about 0.2–1 part by weight of water per part of sodium percarbonate.

In a further embodiment the invention hydrogen peroxide-releasing formulation contains between about 0.05–2 weight percent of a stabilizer ingredient such as sodium silicate, magnesium silicate or magnesium sulfate.

The polyalkylene glycol ingredient of an invention formulation preferably is selected from liquid oxyalkylated diols which have a molecular weight in the range between about 200–8000. Polyethylene glycols are commercially available under tradenames such as Carbowax 200, 300, 400, 600, 900, 1000, 2000, 4000, 6000 and 8000 (Union Carbide), in which the number values are approximations of average molecular weight. Polyethylene-propylene glycols are commercially available under tradenames such as Pluracare/Pluronic L-31 and L-35 (BASF).

The polyalkylene glycol ingredient serves as a hydrophilic vehicle for the other formulation ingredients, and it enhances the compatibility of the ingredients when the formulation is incorporated as a constituent in a detergent or dentifrice composition.

The sodium percarbonate ingredient of an invention formulation is employed in the form of a crystalline powder, which preferably has an average particle size between about 20–600 microns. Methods of manufacturing sodium percarbonate are described in technical publications such as U.S. Pat. No. 4,966,762 and references cited therein.

The colloidal silica ingredient of an invention formulation can be selected from amorphous silica compounds which function as a thickening agent relative to the polyalkylene glycol ingredient. Commercial colloidal silica compounds are available under tradenames such as Sylodent 15 and Sylodent 2 (W. R. Grace), Aerosil 200 (Degussa) and Cabosil fumed silica (Cabot). The colloidal silica ingredient is compatible with the polyalkylene glycol ingredient.

Aerosil 200 is a preferred type of hydrophilic fumed silica having a surface area of about 200 $M^2/g$, and an average particle size between about 10–12 nanometers. Aerosil R972 is a hydrophobic fumed silica having a surface area of about 100 $M^2/g$, and an average particle size of about 15 nanometers.

The alkali metal pyrophosphate ingredient is selected from suitable inorganic salts which include dialkali metal pyrophosphate and tetraalkali metal pyrophosphate and mixtures thereof in a hydrated or unhydrated form. Illustrative of pyrophosphate salts are $Na_2H_2P_2O_7$, $Na_4P_2O_7$ and $K_4P_2O_7$. A typical range of alkali metal pyrophosphate ingredient content is between about 0.5–8 weight percent.

If tetrasodium pyrophosphate is employed as the salt ingredient, preferably it is employed in the form of an anhydrous crystalline powder ($Na_4P_2O_7$) which contributes multiple advantages to an invention formulation. A tetrasodium pyrophosphate ingredient provides an alkalinity which neutralizes the acidity of the colloidal silica ingredient, and prevents an acid-base reaction with the basic sodium percarbonate ingredient. A tetrasodium pyrophosphate ingredient also can function as a chelating agent for polyvalent metals such as iron or manganese which catalyze the decomposition of sodium percarbonate with a resultant loss of active oxygen.

As a further advantage, when an invention formulation is incorporated as a constituent of a dentifrice composition, a pyrophosphate salt such as tetrasodium pyrophosphate ingredient functions an anti-tartar agent.

A present invention hydrogen peroxide-releasing formulation can be blended with other ingredients to form a powder detergent composition, which can include builder, surfactant, optical brightener, perfume, and other conventional detergent constituents.

A present invention hydrogen peroxide-releasing formulation also can be formed into a toothpaste by blending the formulation with dentifrice ingredients, such as sodium bicarbonate, flavorant, sweetener, and the like.

Suitable flavorants include oils of spearmint, peppermint, wintergreen, sassafras, clove, sage, eucalyptus, marjoram and cinnamon, and flavorants such as methyl salicylate and menthol.

Suitable sweeteners include sodium saccharin, sodium cyclamate, xylitol, perillartine, D-tryptophan, aspartame, and the like.

A present invention hydrogen peroxide-releasing formulation can be prepared conveniently by blending each of the particulate ingredients into the polyalkylene glycol ingredient, which normally is a viscous liquid at room temperature. Depending on the relative proportions of ingredients, the formulation product will be a homogenous two-phase suspension in a liquid or gel form at 25° C. As an alternative means of preparation, each of the particulate ingredients can be blended into a separate portion of the polyalkylene glycol medium, and the separate portions then are combined to form the formulation product.

As an alternative ingredient to sodium percarbonate, the present invention also contemplates the use of other inorganic peroxyhydrate compounds which yield hydrogen peroxide when dissolved in an aqueous medium, such as sodium pyrophosphate peroxyhydrate.

The following examples are further illustrative of the present invention. The components and specific ingredients are presented as being typical, and various modifications can be derived in view of the foregoing disclosure within the scope of the invention.

For test purposes in Example I, the level of active oxygen content retained in each formulation under simulated storage conditions is determined as follows:

A 1–2 gram sample of a formulation is weighted accurately, and transferred into 250 ml Erlenmeyer flask. A 75–100 ml aliquot of 3M sulfuric acid is added dropwise while the flask contents are swirled gently. The acidified aqueous medium then is titrated with 0.1N $KMnO_4$ solution until a permanent pink color is evident.

$$\text{active oxygen} = \frac{V \times N \times 0.8}{\text{Sample weight (grams)}}$$

where V is ml of $KMnO_4$ solution consumed; and N is normality of $KMnO_4$ solution.

EXAMPLE I

This Example illustrates the stability of hydrogen peroxide-releasing formulations in accordance with the present invention.

A series of gel formulations are prepared by blending the ingredients listed in the Table.

Figure 1:
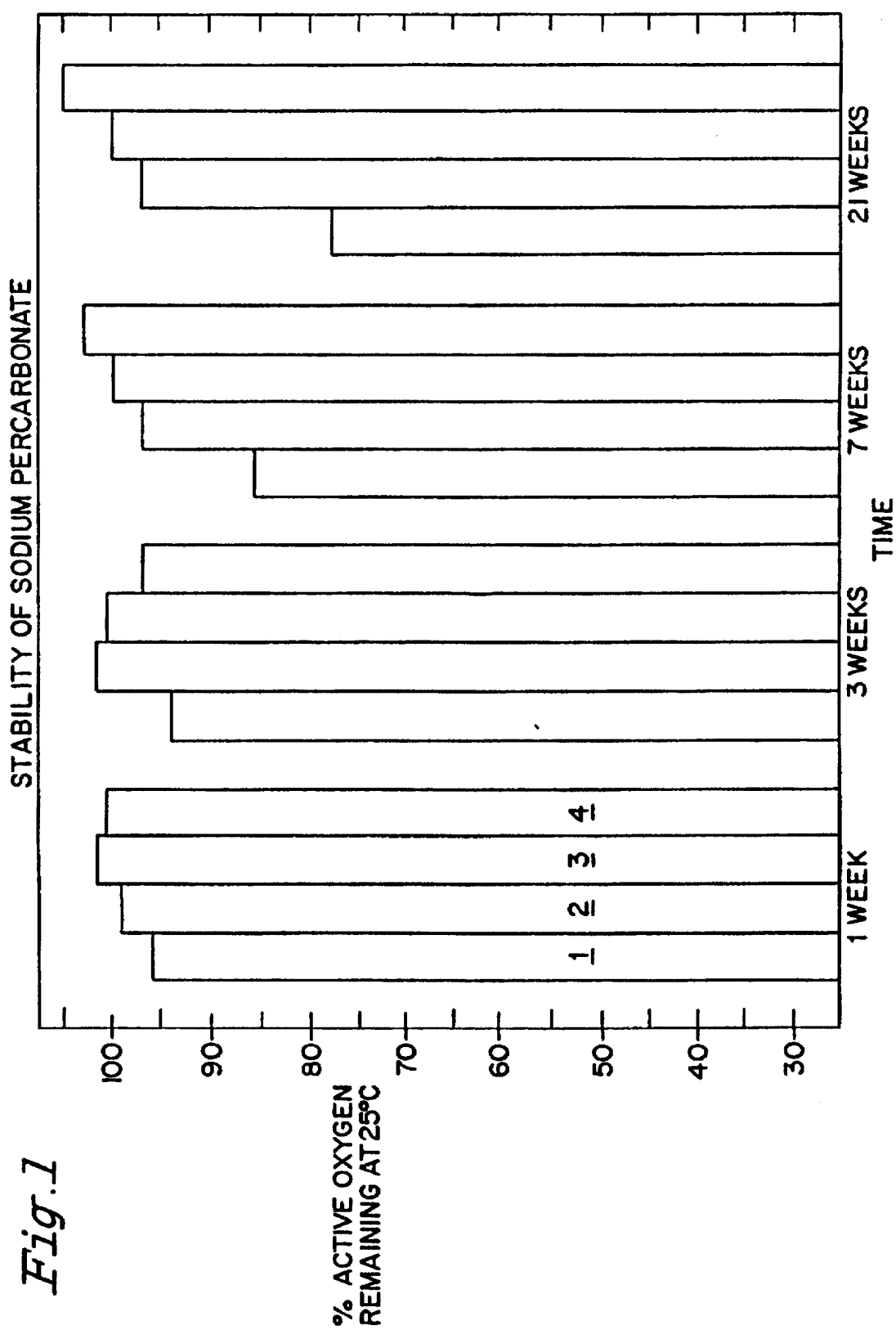
FIGS. 1–3 are bar graphs which are a representation of the comparative stability data corresponding to the 14 formulations as prepared and tested in Example I.
Figure 2:
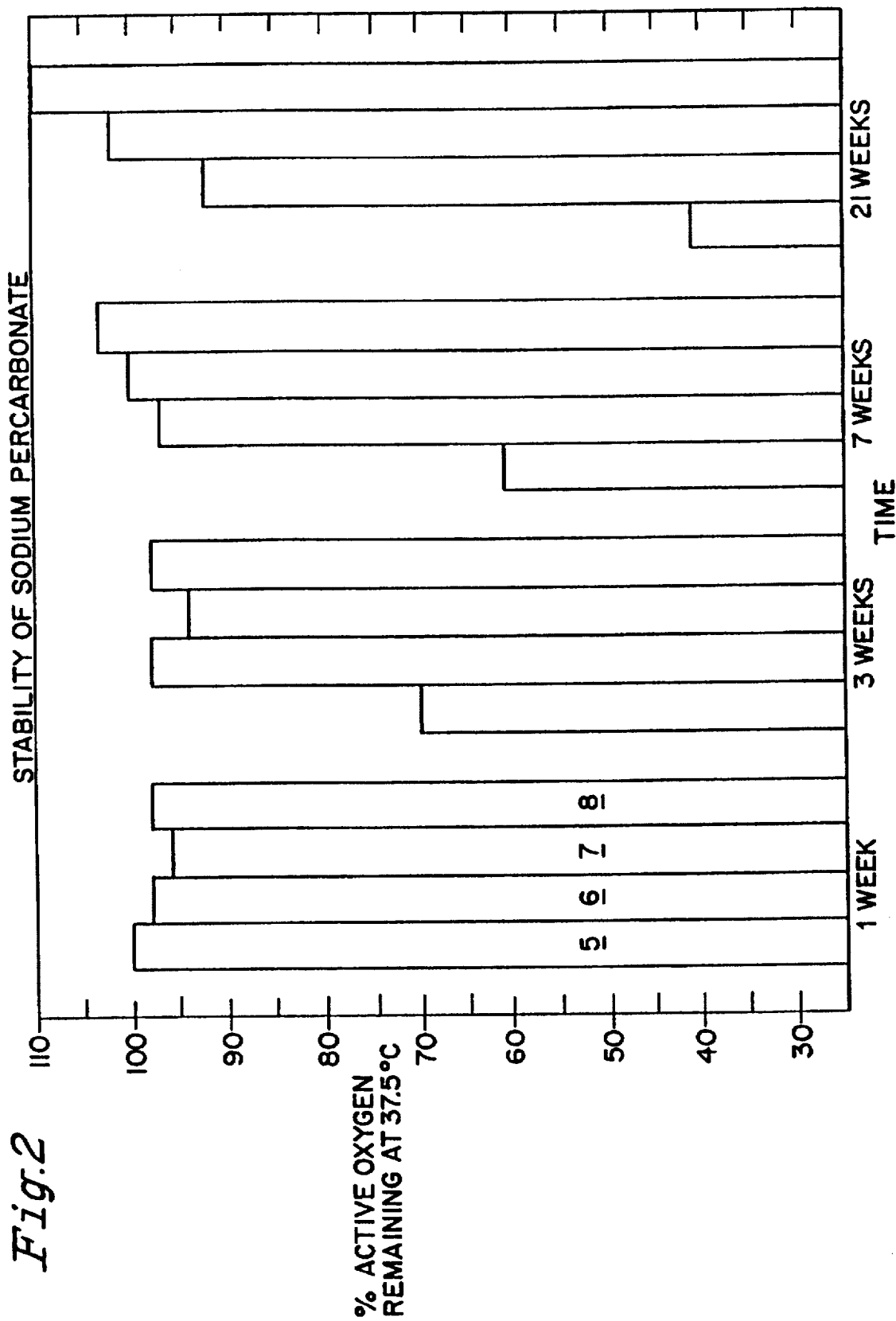
Figure 3:
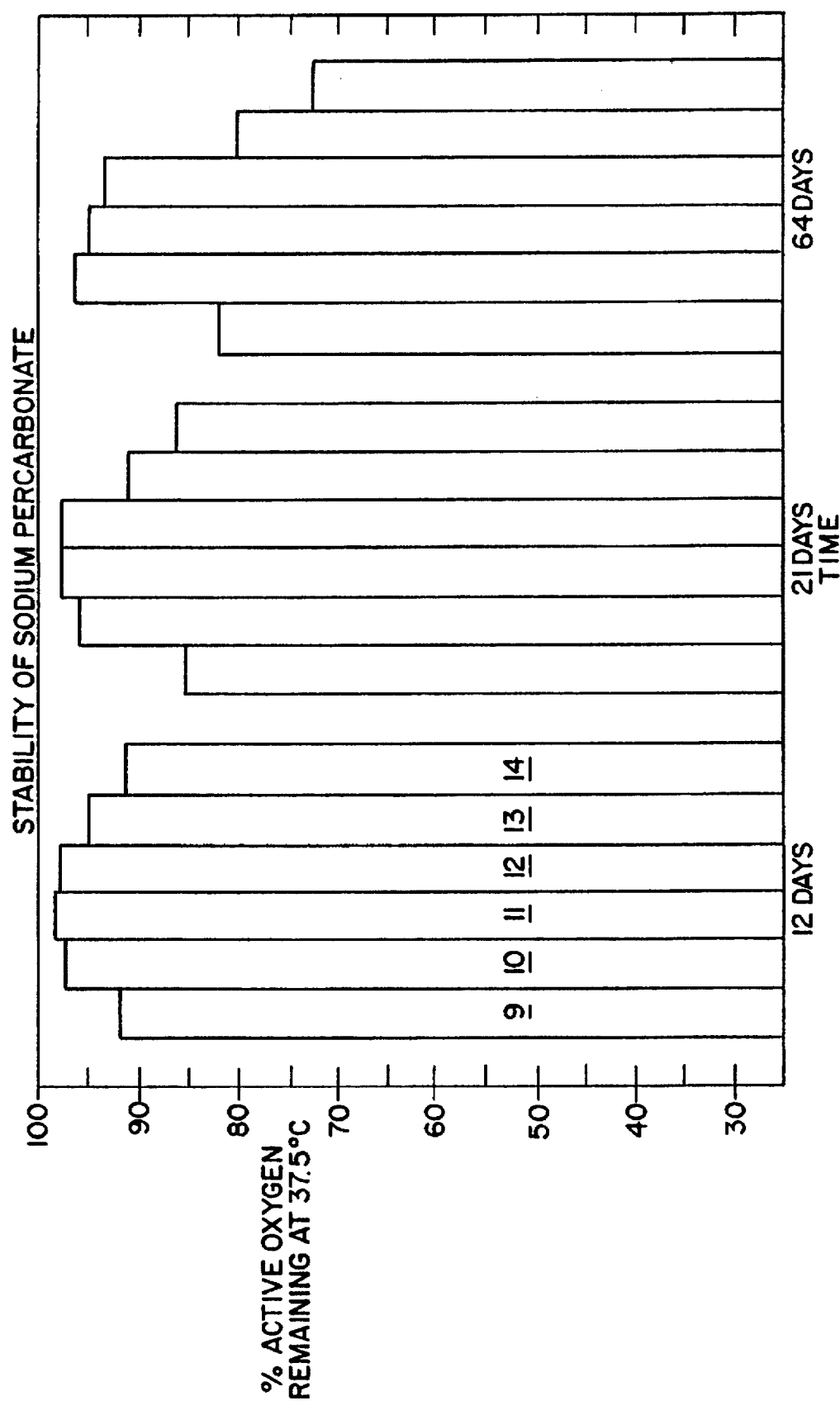

The effect of water content on the stability of sodium percarbonate is tested for the 14 formulations in the Table. FIG. 1–3 are bar graphs which summarize the comparative stability data at temperatures of 25° C. and 37.5° C. over extended periods of time.

The comparative data demonstrate that the highest sodium percarbonate stability is exhibited by gel formulations which have a water content between about 0.2–1 part by weight per part of sodium percarbonate.

TABLE

| Ingredient Parts By Weight | Formulation Numbers | | | | | | | | | | | | | |
|---|---|---|---|---|---|---|---|---|---|---|---|---|---|---|
| | 1 | 2 | 3 | 4 | 5 | 6 | 7 | 8 | 9 | 10 | 11 | 12 | 13 | 14 |
| Polyethylene glycol (M.W. 400) | 34 | 33 | 31 | 29 | 34 | 33 | 31 | 29 | 34 | 32 | 30 | 28 | 26 | 26 |
| Deionized water | 0 | 1 | 3 | 5 | 0 | 1 | 3 | 5 | 0 | 2 | 4 | 6 | 8 | 10 |
| Sodium percarbonate | 6 | 6 | 6 | 6 | 6 | 6 | 6 | 6 | 6 | 6 | 6 | 6 | 6 | 6 |
| Aerosil 200 (Degussa) | 1 | 1 | 1 | 1 | 1 | 1 | 1 | 1 | 1 | 1 | 1 | 1 | 1 | 1 |
| Tetrasodium pyrophosphate | 0.5 | 0.5 | 0.5 | 0.5 | 0.5 | 0.5 | 0.5 | 0.5 | 0.5 | 0.5 | 0.5 | 0.5 | 0.5 | 0.5 |

EXAMPLE II

This Example illustrates the incorporation of a stable hydrogen peroxide-releasing formulation into a heavy duty detergent powder composition in accordance with the present invention.

A pre-blend gel is prepared with the following ingredient:

|  | Parts By Weight |
| --- | --- |
| Polyethylene glycol (M.W. 400) | 30.45 |
| Polyethylene glycol (M.W. 8000) | 0.9 |
| Sodium percarbonate | 6.0 |
| Aerosil 200 (Degussa) | 1.0 |
| Tetrasodium pyrophosphate | 2.0 |
| Water | 6.0 |

The pre-blend is admixed with detergent ingredients to form a heavy duty powder detergent composition with a content of about 2 weight percent of sodium percarbonate. The sodium percarbonate is blended first with sodium carbonate, and then with the other detergent ingredients except for the water. The blended powder is sprayed with water to form granules having an average diameter of 500 microns, and then dried.

Similar results are obtained when tetrapotassium pyrophosphate is employed as the alkali metal pyrophosphate ingredient.

Hydrogen Peroxide-releasing Detergent Composition

|  | Parts By Weight |
| --- | --- |
| Sodium carbonate | 75.0 |
| Sodium Neodol 25-3 sulfate[1] | 4.5 |
| Neodol 25-3 | 2.5 |
| Sodium sulfate | 1.5 |
| Sodium bicarbonate | 1.5 |
| Acusol 912N[2] | 0.5 |
| Sodium carboxymethylcellulose[3] | 0.2 |
| Optical brightener | 0.2 |
| Perfume | 0.1 |
| Water | 7.0 |
| Sodium percarbonate formulation | 16.0 |

[1]Ethoxylated $C_{12}$-$C_{15}$ alcohol sulfate salt (Shell Chemical Company).
[2]Sodium polyacrylate; Rohm & Haas
[3]Finetex Inc.

EXAMPLE III

This Example illustrates the preparation of a stable dentifrice composition in accordance with the present invention.

A pre-blend is prepared with the following ingredients:

|  | Parts By Weight |
| --- | --- |
| Polyethylene glycol (M.W. 400) | 30.45 |
| Polyethylene glycol (M.W. 8000) | 0.9 |
| Sodium percarbonate | 6.0 |
| Aerosil 200 (Degussa) | 1.0 |
| Tetrasodium pyrophosphate | 6.0 |
| Water | 6.0 |

The pre-blend is admixed with additional ingredients to form a composition with a toothpaste consistency:

|  | Weight Percent |
| --- | --- |
| Polyethylene glycol (M.W. 400) | 30.45 |
| Polyethylene glycol (M.W. 8000) | 0.9 |
| Sodium percarbonate | 6.0 |
| Aerosil 200 (Degussa) | 1.0 |
| Tetrasodium pyrophosphate | 6.0 |
| Water | 6.0 |
| Sodium bicarbonate | 48.0 |
| Flavor | 0.75 |
| Saccharin | 0.9 |

The invention toothpaste is more stable than control toothpastes which have a water content of one weight percent and zero weight percent respectively, when tested at 37.5° C. for 21 days. The invention toothpaste has an active oxygen loss of about 4%, and the control toothpastes have an active oxygen loss in the range of about 10–14 percent.

Similar results are obtained with corresponding formulations which have a tetrasodium pyrophosphate content of 0.0, 0.5, 1.0, 2.0, 3.0, 5.0, 8.0 or 12.0 weight percent, respectively. The preferred range of tetrasodium pyrophosphate is between about 0.5–8 weight percent.

What is claimed is:

1. A toothpaste or gel dentifrice composition having incorporated therein formulation ingredients comprising (1) between about 55–90 weight percent of polyalkylene glycol; (2) between about 5–20 weight percent of sodium percarbonate; (3) between about 0.5–6 weight percent of colloidal silica; (4) between about 0–12 weight percent of alkali metal pyrophosphate and (5) between about 0.2–1 part by weight of water per part of sodium percarbonate.

2. A dentifrice composition in accordance with claim 1 wherein the content of alkali metal polyphosphate ingredient is between about 0.5–8 weight percent.

3. A dentifrice composition in accordance with claim 1 wherein the polyalkylene glycol is polyethylene glycol, and the alkali metal pyrophosphate is tetrasodium pyrophosphate.

4. A dentifrice composition in accordance with claim 1 wherein the sodium percarbonate ingredient has an average particle size between about 20–600 microns.

5. A dentifrice composition in accordance with claim 1 wherein the sodium percarbonate ingredient has an active oxygen content between about 8–14 weight percent.

6. A dentifrice composition in accordance with claim 1 which additional contains between about 0.05–2 weight percent of a stabilizer ingredient.

* * * * *